(12) United States Patent
Klostermann et al.

(10) Patent No.: US 9,745,251 B2
(45) Date of Patent: Aug. 29, 2017

(54) LIPASE-STABLE THICKENING AGENT

(71) Applicant: EVONIK INDUSTRIES AG, Essen (DE)

(72) Inventors: Michael Klostermann, Essen (DE); Hans Henning Wenk, Muelheim an der Ruhr (DE); Hans-Juergen Koehle, Mainhausen (DE); Joachim Venzmer, Essen (DE); Dirk Kuppert, Aschaffenburg (DE); Juergen Lattich, Nidderau-Ostheim (DE); Ulrike Kottke, Linsengericht-Grossenhausen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/413,875

(22) PCT Filed: Mar. 7, 2013

(86) PCT No.: PCT/EP2013/054568
§ 371 (c)(1),
(2) Date: Jan. 9, 2015

(87) PCT Pub. No.: WO2014/009027
PCT Pub. Date: Jan. 16, 2014

(65) Prior Publication Data
US 2015/0203443 A1    Jul. 23, 2015

(30) Foreign Application Priority Data
Jul. 11, 2012   (DE) .................. 10 2012 212 085

(51) Int. Cl.
| | | |
|---|---|---|
| *C07C 235/08* | (2006.01) | |
| *C07C 235/10* | (2006.01) | |
| *C11D 1/52* | (2006.01) | |
| *C11D 17/00* | (2006.01) | |
| *A61K 8/42* | (2006.01) | |
| *A61K 8/66* | (2006.01) | |
| *A61Q 5/02* | (2006.01) | |
| *A61Q 5/12* | (2006.01) | |
| *A61Q 19/10* | (2006.01) | |
| *A61Q 5/00* | (2006.01) | |

(52) U.S. Cl.
CPC .............. *C07C 235/08* (2013.01); *A61K 8/42* (2013.01); *A61K 8/66* (2013.01); *A61Q 5/006* (2013.01); *A61Q 5/02* (2013.01); *A61Q 5/12* (2013.01); *A61Q 19/10* (2013.01); *C07C 235/10* (2013.01); *C11D 1/523* (2013.01); *C11D 17/003* (2013.01); *A61K 2800/30* (2013.01); *A61K 2800/48* (2013.01); *A61K 2800/59* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 2,773,852 | A | 12/1956 | Rowe et al. |
| 2,986,517 | A | 5/1961 | Odell et al. |
| 3,234,258 | A | 2/1966 | Morris |
| 3,264,281 | A | 8/1966 | Applewhite et al. |
| 3,977,894 | A | 8/1976 | White et al. |
| 5,075,041 | A | 12/1991 | Lutz |
| 6,211,139 | B1 | 4/2001 | Keys et al. |
| 2006/0047046 | A1 | 3/2006 | Haas |
| 2006/0091578 | A1 | 5/2006 | Bravo et al. |
| 2006/0211831 | A1 | 9/2006 | Nishiguchi et al. |
| 2011/0251294 | A1 | 10/2011 | Weiss et al. |

FOREIGN PATENT DOCUMENTS

| | | |
|---|---|---|
| CN | 1237899 A | 12/1999 |
| DE | 2434147 A1 | 2/1975 |
| DE | 19827304 A1 | 2/1999 |
| EP | 0574277 A1 | 12/1993 |
| EP | 0596209 A2 | 5/1994 |
| EP | 2108036 | 10/2009 |
| EP | 2 273 966 | 1/2011 |
| EP | 2365050 A1 | 9/2011 |
| JP | S58-217598 A | 12/1983 |
| JP | 5-287258 A | 11/1993 |
| JP | 6271445 A | 9/1994 |
| JP | 2004-026781 A | 1/2004 |
| JP | 2006257268 A | 9/2006 |
| JP | 2013523890 A | 6/2013 |
| WO | WO 90/13533 A1 | 11/1990 |
| WO | 9421595 A1 | 9/1994 |
| WO | WO 95/31961 A1 | 11/1995 |
| WO | WO9740005 | 10/1997 |
| WO | WO 98/13017 A1 | 4/1998 |
| WO | WO 01/46373 A1 | 6/2001 |

(Continued)

OTHER PUBLICATIONS

International Search Report dated May 28, 2013 issued in PCT/EP2013/054568.
Nelson Jane S. et al., "Castor-Based Derivatives: Synthesis of Some Acrylate Esters", Journal of the American Oil Chemists' Society (Jan. 1, 1965), pp. 542-545
Schrader, K., "Grundlagen and Rezepturen der Kosmetika [Fundamentals and formulations of cosmetics]", 2nd edition, pp. 329 to 341, Hüthig Buch Verlag Heidelberg, 1989.

(Continued)

*Primary Examiner* — Sudhakar Katakam
*Assistant Examiner* — Jennifer C Sawyer
(74) *Attorney, Agent, or Firm* — Scully, Scott, Murphy & Presser, P.C.

(57) ABSTRACT

The invention relates to novel compounds, to aqueous, in particular surfactant-containing formulations containing the novel compounds and to the use of the novel compounds as thickening agents of aqueous, in particular surfactant-containing formulations.

7 Claims, 8 Drawing Sheets

(56) References Cited

FOREIGN PATENT DOCUMENTS

Figure 1:
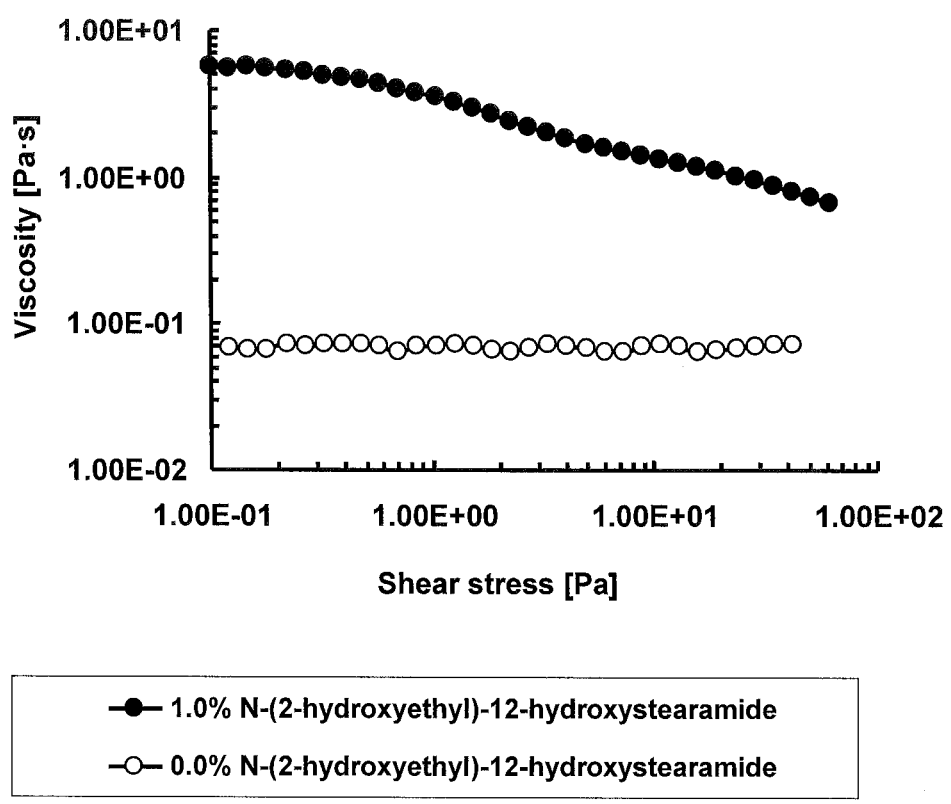

| WO | WO 2008/057455 A2 | 5/2008 |
|---|---|---|
| WO | WO 2009/138306 A1 | 11/2009 |
| WO | WO 2010/056270 A1 | 5/2010 |
| WO | WO 2011/130362 A1 | 10/2011 |

OTHER PUBLICATIONS

Chinese Office Action dated Nov. 17, 2015 from related Chinese Patent Application No. 201380036849.8, together with an English language translation.

Japanese Office Action dated Sep. 13, 2016 received in a corresponding foreign application together with an English-language translation thereof.

LIPASE-STABLE THICKENING AGENT

FIELD OF THE INVENTION

The invention relates to novel compounds, to aqueous, in particular surfactant-containing formulations comprising the novel compounds, and to the use of the novel compounds as thickeners of aqueous, in particular surfactant-containing formulations.

PRIOR ART

A classic thickener for surface-active systems such as, for example, liquid detergents, is hydrogenated castor oil.

EP0596209 discloses crosslinked castor oil derivatives which are likewise used as thickeners.

In modern detergents, lipases, esterases and/or proteases are often used as cleaning boosters. As described in EP2365050, the use of hydrogenated castor oil, however, is not possible in combination with lipases since it is cleaved by the enzyme and consequently the thickening property is lost.

U.S. Pat. No. 2,773,852 describes N-(2-hydroxypropyl)-12-hydroxystearamide as antistatic additive in plastics.

The use of N-(2-hydroxyethyl)-12-hydroxystearamide in a variety of applications has already been reported in a series of patent specifications. Thus, this substance is described for example in WO 2010056270 as additive in polymer composites, in U.S. Pat. No. 6,211,139 as surface-active additive in aqueous polyquat formulations or in DE 2434147 as rheological additive in non-aqueous formulations. By contrast, the use of N-(2-hydroxyethyl)-12-hydroxystearamide has hitherto not been described as a thickener for aqueous formulations.

JP 2004-026781 describes N—(N,N-dimethyl-3-aminopropyl)-12-hydroxystearamide and N—(N,N-diethyl-2-aminoethyl)-12-hydroxystearamide as conditioning agent in haircare applications.

U.S. Pat. No. 3,977,894 discloses the use of N-(2-aminoethyl)-12-hydroxystearamide as additive for organomodified, clay-mineral-based thickeners for nonpolar, nonaqueous systems. Moreover, WO 01/46373 discloses the product of the reaction of hydrogenated castor oil with ethylenediamine and its use as oil phase thickener.

U.S. Pat. No. 2,986,517 reports on the use of N,N-di-(2-hydroxyethyl)-12-hydroxystearamide as rheological additive in lubricating oils.

It was the object of the invention to provide a thickener with shear-thinning properties which, moreover, is lipase-stable.

DESCRIPTION OF THE INVENTION

Surprisingly, it has been found that the amides described below based on 12-hydroxystearic acid are exceptional thickeners for aqueous, in particular surfactant-containing, formulations and, moreover, are not broken down by lipases.

A subject matter of the present invention is therefore certain amides of 12-hydroxystearic acid.

A further subject matter is aqueous formulations comprising certain amides of 12-hydroxystearic acid.

Yet another subject matter of the invention is the use of certain amides of 12-hydroxystearic acid as thickeners of aqueous formulations.

One advantage of the present invention is that with it it is possible to establish, in a targeted manner, a shear-thinning rheological behaviour of the medium to be thickened.

It is a further advantage of the present invention that it is characterized by a complete stability towards lipases.

A particular advantage of amino-functionalized amides of 12-hydroxystearic acid, moreover, is that their thickening properties can be regulated via an adjustment of the pH.

Another advantage of the present invention is the high thickening effect.

Unless stated otherwise, all of the stated percentages (%) are percentages by mass.

The present invention therefore comprises a compound of the general formula (I)

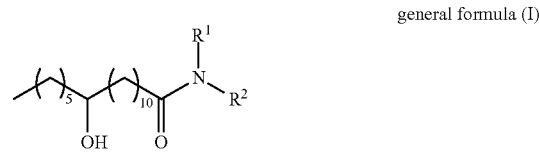

general formula (I)

where $R^1$ is selected from H or an alkyl radical having 1 to 6 carbon atoms that is optionally substituted by OH or amino groups and/or interrupted with oxygen or amino groups and where $R^2$ is selected from H or an alkyl radical having 1 to 6 carbon atoms that is optionally substituted by OH or amino groups and/or interrupted with oxygen or amino groups, with the proviso that compounds where $R^1$=H or 2-hydroxypropyl and $R^2$=H or 2-hydroxypropyl, where one of both $R^1$ or $R^2$=H, =H or N,N-dimethyl-3-aminopropyl and $R^2$=H or N,N-dimethyl-3-aminopropyl, where one of both $R^1$ or $R^2$=H, $R^1$=H or N,N-diethyl-2-aminoethyl and $R^2$=H or N,N-diethyl-2-aminoethyl, where one of both $R^1$ or $R^2$=H, $R^1$=H or 2-hydroxyethyl and $R^2$=H or 2-hydroxyethyl, $R^1$=H or 2-aminoethyl and $R^2$=H or 2-aminoethyl, where one of both $R^1$ or $R^2$=H are excluded.

According to the invention, preference is given to a compound of the general formula (I), where $R^1$=H or N-(2-hydroxyethyl)aminoethyl and $R^2$=N-(2-hydroxyethyl)aminoethyl, where $R^1$ preferably =H, $R^1$=H or 2-(2-hydroxyethoxy)ethyl and $R^2$=2-2-(2-hydroxyethm)ethyl, where $R^1$ preferably =H, $R^1$=methyl or 2,3,4,5,6-pentahydroxyhexyl and $R^2$=2,3,4,5,6-pentahydroxyhexyl, where $R^1$ preferably =methyl and $R^1$=H or 2-(1-piperazinyl)ethyl and $R^2$ 2-(1-piperazinyl)ethyl, where $R^1$ preferably =H.

Compounds of the general formula (I) can for example be synthesized by amidating hydrogenated castor oil with a substituted alkylamine with acidic or alkaline catalysis; a corresponding process is described for example in DE 19827304. The glycerol that is formed during this process can remain in the product or can be removed, at least partially, by distillation. Alternatively, it is also possible to use an alkyl ester of hydrogenated castor oil as fatty component, in which case the alkyl alcohol that is liberated during the amidation can be separated off by distillation.

A further possible synthesis route is the direct amidation of 12-hydroxystearic acid with substituted alkylamines, optionally with acidic catalysis, in which case the resulting condensate is separated off by distillation; such processes are described in EP 2108036 and EP 0574277.

A further subject matter of the present invention is an aqueous formulation comprising at least one compound of the general formula (I)

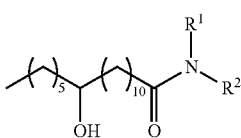

general formula (I)

where $R^1$ is selected from H or an alkyl radical having 1 to 6 carbon atoms that is optionally substituted by OH or amino groups and/or interrupted with oxygen or amino groups and where $R^2$ is selected from H or an alkyl radical having 1 to 6 carbon atoms that is optionally substituted by OH or amino groups and/or interrupted with oxygen or amino groups, with the proviso that the compound where $R^1$=H or N,N-dimethyl-3-aminopropyl and $R^2$=H or N,N-dimethyl-3-aminopropyl, where one of both $R^1$ or $R^2$=H, $R^1$=H or N,N-diethyl-2-aminoethyl and $R^2$=H or N,N-diethyl-2-aminoethyl, where one of both $R^1$ or $R^2$=H, $R^1$=H or 2-hydroxyethyl and $R^2$=H or 2-hydroxyethyl, where one of both $R^1$ or $R^2$=H and $R^1$=H and $R^2$=H is excluded.

The term "aqueous formulation" is to be understood as meaning in particular formulations with a water content of at least 20% by weight, in particular 40% by weight, particularly preferably 60% by weight, based on the total formulation.

Formulations preferred according to the invention are characterized in that the compound of the general formula (I) is selected from those where $R^1$=H or 2-hydroxypropyl and $R^2$=2-hydroxypropyl, where $R^1$ preferably =H, $R^1$=H or 2-aminoethyl and $R^2$=2-aminoethyl, where $R^1$ preferably =H, $R^1$=H or N-(2-hydroxyethyl)aminoethyl and $R^2$=N-(2-hydroxyethyl)aminoethyl, where $R^1$ preferably =H, $R^1$=H or 2-(2-hydroxyethoxy)ethyl and $R^2$=2-2-(2-hydroxyethoxy)ethyl, where $R^1$ preferably =H, $R^1$=methyl or 2,3,4,5,6-pentahydroxyhexyl and $R^2$=2,3,4,5,6-pentahydroxyhexyl, where $R^1$ preferably =methyl and $R^1$=H or 2-(1-piperazinyl)ethyl and $R^2$=2-(1-piperazinyl)ethyl, where $R^1$ preferably =H.

Particularly advantageous formulations have proven to be those which are characterized in that the compound of the general formula (I) is selected from those where $R^1$=H or 2-hydroxypropyl and $R^2$=2-hydroxypropyl, where $R^1$ preferably =H, $R^1$=H or 2-aminoethyl and $R^2$=2-aminoethyl, where $R^1$ preferably =H.

It is preferred according to the invention that at least one compound of the general formula (I) is present in the aqueous formulation in an amount of from 0.1% by weight to 50% by weight, particularly preferably from 0.5% by weight to 25% by weight, where the % by weight refers to the total formulation.

In particular, preference is given to aqueous washing and cleaning formulations, such as e.g. liquid detergents or cosmetic formulations such as liquid soaps, shower gels or shampoos which, besides the compound of the general formula (I), preferably comprise at least one surfactant, where anionic, nonionic, cationic and/or amphoteric surfactants can be used. From the point of view of application, preference is given to mixtures of anionic and nonionic surfactants. The total surfactant content of the aqueous formulation is preferably 5 to 60% by weight and particularly preferably 15 to 40% by weight, based on the total formulation.

As nonionic surfactants, preference is given to using alkoxylated, advantageously ethoxylated, in particular primary alcohols having preferably 8 to 18 carbon atoms and on average 1 to 12 mol of ethylene oxide (EO) per mole of alcohol in which the alcohol radical can be linear or preferably 2-methyl-branched and/or can contain a mixture of linear and methyl-branched radicals, as is customarily present in oxo alcohol radicals. In particular, however, alcohol ethoxylates with linear radicals from alcohols of native origin having 12 to 18 carbon atoms, for example from coconut alcohol, palm alcohol, tallow fatty alcohol or oleyl alcohol, and on average 2 to 8 EO per mole of alcohol are preferred. The preferred ethoxylated alcohols include for example C12-C14-alcohols with 3 EO, 4 EO or 7 EO, C9-C11-alcohol with 7 EO, C13-C15-alcohols with 3 EO, 5 EO, 7 EO or 8 EO, C12-C18-alcohols with 3 EO, 5 EO or 7 EO and mixtures of these, such as mixtures of C12-C14-alcohol with 3 EO and C12-C18-alcohol with 7 EO. The stated degrees of ethoxylation are statistical average values which can be an integer or a fraction for a specific product. Preferred alcohol ethoxylates have a narrowed homologue distribution. In addition to these nonionic surfactants, it is also possible to use fatty alcohols having more than 12 EO. Examples thereof are tallow fatty alcohol having 14 EO, 25 EO, 30 EO or 40 EO. Nonionic surfactants which comprise EO and PO (propylene oxide) groups together in the molecule can also be used. Here, it is possible to use block copolymers with EO-PO block units and/or PO-EO block units, but also EO-PO-EO copolymers and/or PO-EO-PO copolymers.

It is of course also possible to used mixed alkoxylated nonionic surfactants in which EO and PO units are not distributed blockwise, but randomly. Such products are obtainable as a result of the simultaneous action of ethylene oxide and propylene oxide on fatty alcohols.

Furthermore, alkyl glycosides can also be used as further nonionic surfactant.

A further class of preferably used nonionic surfactants, which are used either as the sole nonionic surfactant or in combination with other nonionic surfactants, are alkoxylated, preferably ethoxylated or ethoxylated and propoxylated fatty acid alkyl esters, preferably having 1 to 4 carbon atoms in the alkyl chain, in particular fatty acid methyl esters, as are described for example in the Japanese patent application JP 58/217598 or which are prepared preferably in accordance with the process described in the international patent application WO-A-90/13533.

Nonionic surfactants of the amine oxide type, for example N-cocoalkyl-N,N-dimethylamine oxide and N-tallow-alkyl-N,N-dihydroxyethylamine oxide, and of the fatty acid alkanolamide type may also be suitable. The amount of these nonionic surfactants is preferably not more than that of the ethoxylated fatty alcohols, in particular not more than half thereof.

Further suitable surfactants are polyhydroxy fatty acid amides; the polyhydroxy fatty acid amides are substances which can usually be obtained by reductive amination of a reducing sugar with ammonia, an alkylamine or an alkanolamine and subsequent acylation with a fatty acid, a fatty acid alkyl ester or a fatty acid chloride.

Anionic surfactants that are used are for example those of the sulphonate and sulphate type. Suitable surfactants of the sulphonate type here are preferably C9-C13-alkylbenzenesulphonates, olefinsulphonates, i.e. mixtures of alkene- and hydroxyalkanesulphonates, and also disulphonates, as are obtained for example from C12-C18-monoolefins with terminal or internal double bond by sulphonation with gaseous sulphur trioxide and subsequent alkaline or acidic hydrolysis of the sulphonation products. Also of suitability are alkanesulphonates which are obtained from C12-C18-alkanes for example by sulphochlorination or sulphoxidation with subsequent hydrolysis or neutralization. The esters of α-sulpho fatty acids (ester sulphonates), for example the α-sulphonated methyl esters of hydrogenated coconut, palm kernel or tallow fatty acids are also likewise suitable.

Further suitable anionic surfactants are sulphated fatty acid glycerol esters. Fatty acid glycerol esters are to be understood as meaning the mono-, di- and triesters, and also mixtures thereof, as are obtained during the production by esterification of a monoglycerol with 1 to 3 mol of fatty acid or during the transesterification of triglycerides with 0.3 to 2 mol of glycerol. Preferred sulphated fatty acid glycerol esters here are the sulphation products of saturated fatty acids having 6 to 22 carbon atoms, for example of caproic acid, caprylic acid, capric acid, myristic acid, lauric acid, palmitic acid, stearic acid or behenic acid.

Preferred alk(en)yl sulphates are the alkali metal and in particular the sodium salts of the sulphuric acid half-esters of the C12-C18-fatty alcohols, for example of coconut fatty alcohol, tallow fatty alcohol, lauryl, myristyl, cetyl or stearyl alcohol or of the C10-C20-oxo alcohols and those half-esters of secondary alcohols of these chain lengths.

Furthermore, preference is given to alk(en)yl sulphates of the specified chain length which contain a synthetic straight-chain alkyl radical produced on a petrochemical basis which have an analogous degradation behaviour to the equivalent compounds based on fatty chemical raw materials. From the point of view of washing, the C12-C16-alkyl sulphates and C12-C18-alkyl sulphates and also C14-C18-alkyl sulphates are preferred. 2,3-Alkyl sulphates, which are prepared for example in accordance with the U.S. Pat. No. 3,234,258 or 5,075,041 and can be obtained as commercial products of the Shell Oil Company under the name DAN®, are also suitable anionic surfactants.

The sulphuric acid monoesters of the straight-chain or branched C7-C20-alcohols ethoxylated with 1 to 6 mol of ethylene oxid, such as 2-methyl-branched C9-C11-alcohols having on average 3.5 mol of ethylene oxide (EO) or C12-C18-fatty alcohols with 1 to 4 EO, are also suitable. They are used in cleaning compositions only in relatively small amounts, for example in amounts of from 1 to 5% by weight, on account of their high foaming behaviour.

Further suitable anionic surfactants are also the salts of alkylsulphosuccinic acid, which are also referred to as sulphosuccinates or as sulphosuccinic acid esters and are the monoesters and/or diesters of sulphosuccinic acid with alcohols, preferably fatty alcohols and in particular ethoxylated fatty alcohols. Preferred sulphosuccinates comprise C8-C18-fatty alcohol radicals or mixtures of these. Particularly preferred sulphosuccinates comprise a fatty alcohol radical which is derived from ethoxylated fatty alcohols. In this connection, particular preference is in turn given to sulphosuccinates whose fatty alcohol radicals are derived from ethoxylated fatty alcohols with a narrow homologue distribution. It is also likewise possible to use alk(en)ylsuccinic acid having preferably 8 to 18 carbon atoms in the alk(en)yl chain or salts thereof.

Particularly preferred anionic surfactants are soaps. Saturated and unsaturated fatty acid soaps, such as the salts of lauric acid, myristic acid, palmitic acid, stearic acid, (hydrogenated) erucic acid and behenic acid, and also in particular soap mixtures derived from natural fatty acids, for example coconut, palm kernel, olive oil or tallow fatty acids, are suitable.

The anionic surfactants including the soaps can be present in the form of their sodium, potassium or ammonium salts, and also as soluble salts of organic bases, such as mono-, di- or triethanolamine. Preferably, the anionic surfactants are present in the form of their sodium or potassium salts, in particular in the form of the sodium salts.

According to the invention, amphoteric surfactants which can be used are those surface-active compounds which carry at least one quaternary ammonium group and at least one —COO— or —SO3- group in the molecule. Particularly preferred amphoteric surfactants in this connection are betaine surfactants such as alkyl- or alkylamidopropylbetaines. In particular, preference is given here to betaines such as the N-alkyl-N,N-dimethylammonium glycinates, e.g. cocoalkyldimethylammonium glycinate, N-acylaminopropyl-N,N-dimethylammonium glycinates, e.g. cocoacylaminopropyldimethylammonium glycinate, C12-C18-alkyldimethylacetobetaine, cocoamidopropyldimethylacetobetaine, 2-alkyl-3-carboxymethyl-3-hydroxyethylimidazolines and sulphobetaines having in each case 8 to 18 carbon atoms in the alkyl or acyl group and also cocoacylaminoethyl hydroxyethylcarboxymethylglycinate. A particularly preferred zwitterionic surfactant is the N,N-dimethyl-N-(lauroylamidopropyl)ammonium acetobetaine known under the INCI name Cocamidopropyl Betaine.

Further suitable amphoteric surfactants are the group of amphoacetates and amphodiacetates, in particular for example coco- or laurylamphoacetates or -diacetates, the group of amphopropionates and amphodipropionates, and also the group of amino-acid-based surfactants such as acyl glutamates, in particular disodium cocoyl glutamate and sodium cocoyl glutamate, acyl glycinates, in particular cocoyl glycinate, and acyl sarcosinates, in particular ammonium lauroyl sarcosinate and sodium cocoyl sarcosinate.

In one alternative embodiment of the formulation according to the invention, the surfactant is biosurfactants, in particular glycolipids, with rhamnolipids, sophorolipids, trehalose other mycolic-acid-containing glycolipids, and also cellobiose and mannosylerythritol lipids being preferred, sophorolipids and rhamnolipids being particularly preferred and sophorolipids being very particularly preferred. In this connection, it may in particular be advantageous if the formulation additionally comprises a surfactant from the group of linear alkylbenzenesulphonates (LAS), in particular selected from benzenesulphonic acid, dodecylbenzenesulphonic acid, benzenesulphonic acid C10-13-alkyl derivatives, n-alkyl(C10-C13)benzenesulphonates, benzenesulphonic acid dodecyl ester, and also the sodium salts of the aforementioned acids, particularly preferably sodium n-C10-13-alkylbenzenesulphonate.

In addition to the at least one compound of the general formula (I) and the at least one surfactant, the aqueous formulations can comprise further ingredients which further improve the application and/or aesthetic properties of the aqueous formulations. As a rule, preferred formulations comprise, in addition to the at least one compound of the general formula (I) and the at least one surfactant, one or more substances selected from the groups of builders, bleaches, bleach activators, enzymes, electrolytes, nonaqueous solvents, pH extenders, fragrances, in particular encapsulated fragrances, perfume carriers, fluorescent agents, dyes, hydrotopes, foam inhibitors, silicone oils, modified siloxanes, such as organomodified siloxanes, amino- and polyether-functional and cationic siloxanes, antiredeposition agents, optical brighteners, greying inhibitors, shrink preventers, crease protectants, colour transfer inhibitors, antimicrobial active ingredients, germicides, fungicides, antioxidants, corrosion inhibitors, antistats, ironing aids, phobicization and impregnation agents, deposition polymers, cationic, amino-functional or zwitterionic polymers, swelling and nonslip agents, and also UV absorbers.

Cosmetic care and cleansing formulations according to the invention can for example comprise at least one additional component selected from the group of
emollients,
emulsifiers,
thickeners/viscosity regulators/stabilizers,
antioxidants,
hydrotropes (or polyols),
solids and fillers,
pearlescent additives,
deodorant and antiperspirant active ingredients,
insect repellents,
self-tanning agents,
preservatives,
conditioners,
perfumes,
dyes,
cosmetic active ingredients,
care additives,
superfatting agents,
solvents.

Substances which can be used as exemplary representatives of the individual groups are known to the person skilled in the art and can be found for example in EP2273966A1. This patent application is hereby incorporated by reference and thus forms part of the disclosure.

As regards further optional components and the amounts of these components used, reference is made expressly to the relevant handbooks known to the person skilled in the art, for example K. Schrader, "Grundlagen and Rezepturen der Kosmetika [Fundamentals and formulations of cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures from the manufacturers of the particular basic substances and active ingredients. These existing formulations can usually be adopted without change. If necessary, however, the desired modifications can be undertaken without complication for the purposes of adaptation and optimization by means of simple experiments.

Since the present invention concerns lipase-stable thickeners, it is particularly preferred that the formulation according to the invention comprises at least one enzyme in addition to the at least one compound of the general formula (I).

Suitable enzymes are in particular those from the classes of the hydrolases, preferably proteases, esterases, lipases, lipolytic enzymes, amylases, cellulases and other glycosyl hydrolases and mixtures of said enzymes.

All of these hydrolases contribute during washing to the removal of stains such as protein-, grease- or starch-containing stains and greying. Moreover, cellulases and other glycosyl hydrolases can contribute to colour retention and to increasing the softness of the textile by removing pilling and microfibrils. For bleaching and/or for inhibiting colour transfer, oxireductases can also be used. Enzymatic active ingredients obtained from bacterial strains or fungi such as *Bacillus subtilis, Bacillus licheniformis, Streptomyceus griseus* and *Humicola insolens* are particularly well-suited. Preference is given to using proteases of the subtilisin type and in particular proteases which are obtained from *Bacillus lentus*. In this connection, enzyme mixtures, for example of protease and amylase or protease and lipase or lipolytic enzymes or protease and cellulase or of cellulase and lipase or lipolytic enzymes or of protease, amylase and lipase or lipolytic enzymes or protease, lipase or lipolytic enzymes and cellulase, but in particular protease and/or lipase-containing mixtures or mixtures with lipolytic enzymes are of particular interest. Examples of such lipolytic enzymes are the known cutinases. Peroxidases or oxidases have also proven to be suitable in some cases. Suitable amylases include in particular alpha-amylases, isoamylases, pullulanases and pectinases. As cellulases, preference is given to using cellobiohydrolases, endoglucanases and β-glucosidases, which are also called cellobiases, and mixtures of these. Since different cellulase types differ in respect of their CMCase and avicelase activities, the desired activities can be established though targeted mixtures of the cellulases.

The enzymes can be adsorbed onto carrier substances in order to protect them against premature decomposition. The fraction of enzymes, enzyme mixtures or enzyme granules can be for example about 0.1 to 5% by weight, preferably 0.12 to about 2.5% by weight.

The formulations according to the invention can be prepared by known processes, in particular and preferably they can be prepared by the process according to the invention described below:

A further subject matter of the present invention is a process for the preparation of thickened, aqueous formulations comprising the process steps:

A) provision of a compound of the general formula (I)

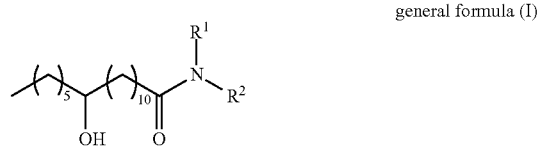

general formula (I)

where $R^1$ is selected from H or an alkyl radical having 1 to 6 carbon atoms that is optionally substituted by OH or amino groups and/or interrupted with oxygen or amino groups and where $R^2$ is selected from H or an alkyl radical having 1 to 6 carbon atoms that is optionally substituted by OH or amino groups and/or interrupted with oxygen or amino groups, B) provision of an aqueous formulation and C) mixing of the compound of the general formula (I) with the aqueous formulation.

With the process according to the invention it is possible to prepare thickened formulations, the term "thickened" in connection with the process according to the invention being understood as meaning that the viscosity, in each case measured at 25° C., of the aqueous formulation of process step C) is increased after carrying out the process according to the invention.

According to the invention, in process step A), preference is given to using compounds of the general formula (I) selected from those where $R^1$=H or 2-hydroxypropyl and $R^2$=2-hydroxypropyl, where $R^1$ preferably =H, $R^1$=H or 2-hydroxyethyl and $R^2$=2-hydroxyethyl, where $R^1$ preferably =H, $R^1$=H or 2-aminoethyl and $R^2$=2-aminoethyl, where $R^1$ preferably =H, $R^1$=H or N-(2-hydroxyethyl)aminoethyl and $R^2$=N-(2-hydroxyethyl)aminoethyl, where $R^1$ preferably =H, $R^1$=H or 2-(2-hydroxyethoxy)ethyl and $R^2$=2-2-(2-hydroxyethoxy)ethyl, where $R^1$ preferably =H, $R^1$=methyl or 2,3,4,5,6-pentahydroxyhexyl and $R^2$=2,3,4,5,6-pentahydroxyhexyl, where $R^1$ preferably =methyl, $R^1$=H or 2-(1-piperazinyl)ethyl and $R^2$=2-(1-piperazinyl)ethyl, where $R^1$ preferably =H and $R^1$=H or N,N-dimethyl-3-aminopropyl and $R^2$=N,N-dimethyl-3-aminopropyl, where $R^1$ preferably =H.

In process step A), it is particularly advantageous to use a compound of the general formula (I) which are characterized in that it is selected from those where $R^1$=H or 2-hydroxypropyl and $R^2$=2-hydroxypropyl, where $R^1$ preferably =H, $R^1$=H or 2-hydroxyethyl and $R^2$=2-hydroxyethyl, where $R^1$ preferably =H, $R^1$=H or 2-aminoethyl and $R^2$=2-aminoethyl, where $R^1$ preferably =H, $R^1$=H or N,N-dimethyl-3-aminopropyl and $R^2$=N,N-dimethyl-3-aminopropyl, where $R^1$ preferably =H.

In process step B), in particular surfactant-containing, aqueous formulations are used. In connection with the present invention, the term "surfactant-containing formulation" is to be understood as meaning formulations which comprise surfactants, in particular the surfactants specified above in connection with the formulations according to the invention, preferably in a concentration of from 5 to 60% by weight and particularly preferably from 15 to 40% by weight, based on the total formulation.

In a preferred embodiment of the process according to the invention for thickening aqueous formulations, in particular for thickening surfactant-containing, aqueous formulations, in process step A), a compound of the general formula (I) is used in the form of a composition having a pH of 0 to 4, in particular of 0.5 to 2, particularly preferably of 0.8 to 1.5, where at least one of the radicals $R^1$ or $R^2$ is an alkyl radical having 1 to 6 carbon atoms substituted with at least one amino group, and in a process step D), the pH of the mixture from C) is increased to a pH range from 5 to 12, particularly preferably to a pH range from 7 to 10.

In connection with the present invention, the pH is to be measured at 25° C. using a calibrated pH electrode in accordance with ISO 4319 (1977).

In this embodiment, in process step A), in particular a compound of the general formula (I) is used which is characterized in that it is selected from those where $R^1$=H or N-(2-hydroxyethyl)aminoethyl and $R^2$=N-(2-hydroxyethyl)aminoethyl, where $R^1$ preferably =H, $R^1$=H or 2-aminoethyl and $R^2$=2-aminoethyl, where $R^1$ preferably =H and $R^1$=H or N,N-dimethyl-3-aminopropyl and $R^2$=N,N-dimethyl-3-aminopropyl, where $R^1$ preferably =H.

The composition comprising the compound of the general formula (I) which is provided in process step A) is in particular an aqueous composition.

In this embodiment, in process step D), the pH is increased by adding a base. Bases that are preferably used are selected from NaOH, KOH, ammonia, monoethanolamine, diethanolamine and triethanolamine, with monoethanolamine being particularly preferred.

In an alternative preferred embodiment of the process according to the invention for thickening aqueous formulations, in particular for thickening surfactant-containing, aqueous formulations, in process step B), the mixing is carried out in a temperature range from 65° C. to 100° C., preferably from 75° C. to 85° C. and in a process step E), the mixture from C) is reduced to a temperature range from 0° C. to 60° C., particularly preferably to a temperature range from 5° C. to 45° C.

In this connection, in process step A), in particular a compound of the general formula (I) is used which is characterized in that it is selected from those where $R^1$=H or 2-hydroxypropyl and $R^2$=2-hydroxypropyl, where $R^1$ preferably =H and $R^1$=H or 2-hydroxyethyl and $R^2$=2-hydroxyethyl, where $R^1$ preferably =H.

A further subject matter of the present invention is the use of a compound of the general formula (I)

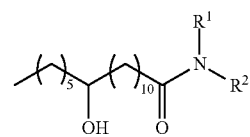

general formula (I)

where $R^1$ is selected from H or an alkyl radical having 1 to 6 carbon atoms that is optionally substituted by OH or amino groups and/or interrupted with oxygen or amino groups and where $R^2$ is selected from H or an alkyl radical having 1 to 6 carbon atoms that is optionally substituted by OH or amino groups and/or interrupted with oxygen or amino groups, for thickening aqueous formulations, in particular for thickening surfactant-containing, aqueous formulations.

According to the invention, preference is given to using compounds of the general formula (I) selected from those where $R^1$=H or 2-hydroxypropyl and $R^2$=2-hydroxypropyl, where $R^1$ preferably =H, $R^1$=H or 2-hydroxyethyl and $R^2$=2-hydroxyethyl, where $R^1$ preferably =H, $R^1$=H or 2-aminoethyl and $R^2$=2-aminoethyl, where $R^1$ preferably =H, $R^1$=H or N-(2-hydroxyethyl)aminoethyl and $R^2$=N-(2-hydroxyethyl)aminoethyl, where $R^1$ preferably =H, $R^1$=H or 2-(2-hydroxyethoxy)ethyl and $R^2$=2-2-(2-hydroxyethoxy)ethyl, where $R^1$ preferably =H, $R^1$=methyl or 2,3,4,5,6-pentahydroxyhexyl and $R^2$=2,3,4,5,6-pentahydroxyhexyl, where $R^1$ preferably =methyl, $R^1$=H or 2-(1-piperazinyl)ethyl and $R^2$=2-(1-piperazinyl)ethyl, where $R^1$ preferably =H and $R^1$=H or N,N-dimethyl-3-aminopropyl and $R^2$=N,N-dimethyl-3-aminopropyl, where $R^1$ preferably =H.

In connection with the present invention, the term "surfactant-containing formulation" is to be understood as meaning formulations which in particular comprise the surfactants specified above in connection with the formulations according to the invention, preferably in a concentration of 5 to 60% by weight and particularly preferably from 15 to 40% by weight, based on the total formulation.

It is particularly advantageous to use a compound of the general formula (I) which is characterized in that it is selected from those where $R^1$=H or 2-hydroxypropyl and $R^2$=2-hydroxypropyl, where $R^1$ preferably =H, $R^1$=H or 2-hydroxyethyl and $R^2$=2-hydroxyethyl, where $R^1$ preferably =H, $R^1$=H or 2-aminoethyl and $R^2$=2-aminoethyl, where $R^1$ preferably =H, $R^1$=H or N,N-dimethyl-3-aminopropyl and $R^2$=N,N-dimethyl-3-aminopropyl, where $R^1$ preferably =H.

In a preferred embodiment of the use according to the invention of a compound of the general formula (I) for thickening aqueous formulations, in particular for thickening surfactant-containing, aqueous formulations, at least one of the radicals $R^1$ or $R^2$ is an alkyl radical having 1 to 6 carbon atoms substituted with at least one amino group, where the use according to the invention involves a pH change of the aqueous formulation, in particular a pH increase, preferably to a pH range from 5 to 12, particularly preferably to a pH range from 7 to 10. In this connection, in particular a compound of the general formula (I) is used which is characterized in that it is selected from those where $R^1$=H or N-(2-hydroxyethyl)aminoethyl and $R^2$=N-(2-hydroxyethyl)aminoethyl, where $R^1$ preferably =H, $R^1$=H or 2-aminoethyl and $R^2$=2-aminoethyl, where $R^1$ preferably =H and $R^1$=H or N,N-dimethyl-3-aminopropyl and $R^2$=N,N-dimethyl-3-aminopropyl, where $R^1$ preferably =H.

In an alternative preferred embodiment of the use according to the invention of a compound of the general formula (I) for thickening aqueous formulations, in particular for thickening surfactant-containing, aqueous formulations, the use according to the invention involves a temperature reduction of the aqueous formulation, preferably to a temperature range from 0 to 60° C., particularly preferably to a temperature range from 5 to 45° C. In this connection, in particular a compound of the general formula (I) is used which is characterized in that it is selected from those where $R^1$=H or 2-hydroxypropyl and $R^2$=2-hydroxypropyl, where $R^1$ preferably =H and $R^1$=H or 2-hydroxyethyl and $R^2$=2-hydroxyethyl, where $R^1$ preferably =H.

In the examples given below, the present invention is described by way of example without intending to limit the invention, the scope of application of which arises from the entire description and the claims, to the embodiments specified in the examples. The rheology experiment listed in the examples (viscosity as a function of the shear stress in a shear stress range from 0.1 to 50 Pa) were carried out using an air-supported oscillation rheometer (Stresstech model from Rheologica), with measurement in all cases being carried out using a plate-plate geometry at a gap distance of 1.0 mm. All measurements were carried out at 25° C.

The following figures form part of the examples:

FIG. 1: Rheology profile of a detergent formulation comprising N-(2-hydroxyethyl)-12-hydroxystearamide FIG. 2: Rheology profile of a detergent formulation comprising N-(2-hydroxypropyl-12-hydroxystearamide FIG. 3: Rheology profile of a detergent formulation comprising N-(2-hydroxypropyl)-12-hydroxystearamide (2)

Figure 4:
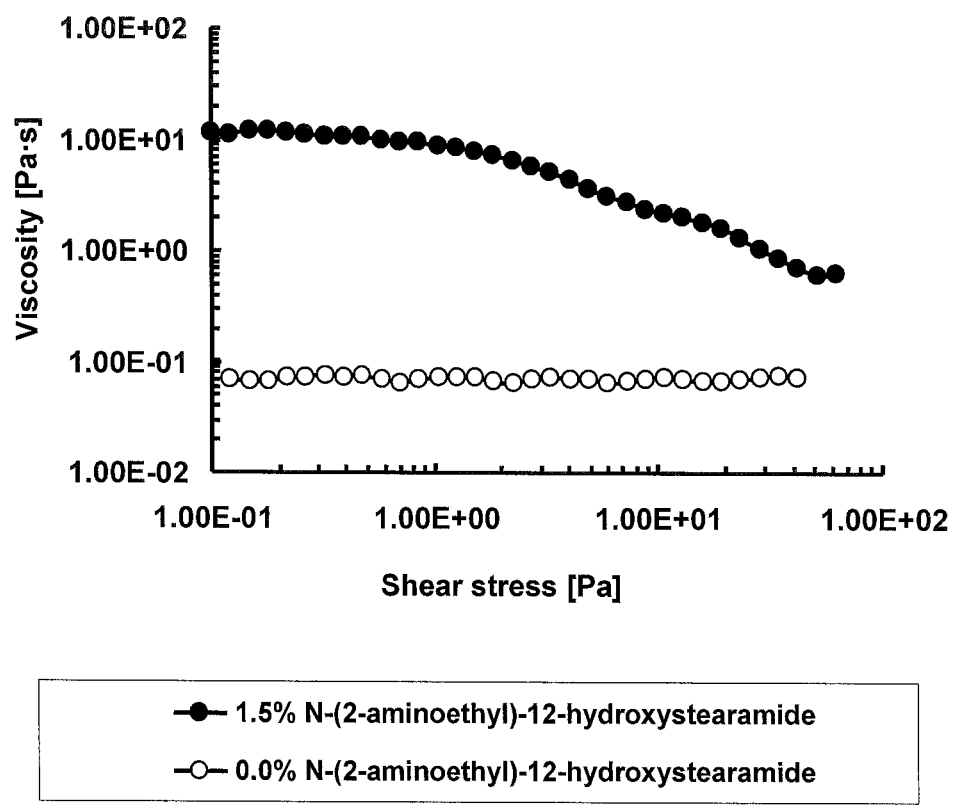

FIG. 4: Rheology profile of a detergent formulation comprising N-(2-aminoethyl)-12-hydroxystearamide FIG. 5: Rheology profile of a detergent formulation comprising N—(N,N-dimethyl-3-aminopropyl)-12-hydroxystearamide FIG. 6: Rheology profile of an aqueous formulation comprising N-(2,3,4,5,6-pentahydroxyhexyl)-12-hydroxystearamide FIG. 7: Rheology profile of a detergent formulation comprising hydrogenated castor oil FIG. 8: Lipase stability of a detergent formulation comprising N-(2-hydroxypropyl)-12-hydroxystearamide compared to hydrogenated castor oil after 60 minutes (8a) and after six days (8b).

EXAMPLES

Example 1: Synthesis of
N-(2-hydroxyethyl)-12-hydroxystearamide 824 g (0.88 mol) of hydrogenated castor oil were admixed, at 90° C. and with stirring, with 161 g (2.64 mol) of 2-hydroxyethylamine and homogenized. This mixture was dried at a vacuum of 50 mbar and a temperature of 90-100° C. for 30 minutes. The vacuum was then broken with nitrogen and 10 g of a 30% strength by weight sodium methanolate solution in methanol were present. The reaction mixture was stirred for 3 hours at 110° C., reaction control taking place via the determination of the free 2-hydroxyethylamine (acid-base titration). 989 g of a N-(2-hydroxyethyl)-12-hydroxystearamide were obtained, the content of free 2-hydroxyethylamine was 1.2% by weight.

Example 2: Synthesis of
N-(2-hydroxypropyl)-12-hydroxystearamide 374.2 g (0.40 mol) of hydrogenated castor oil were mixed as described under Example 1 with 90.1 g (1.2 mol) of 2-hydroxypropylamine and dried. 5 g of a 30% strength by weight sodium methanolate solution were added to this reaction mixture and stirring was carried out for 2.5 hours at 110° C. Reaction control was carried out via the determination of the free 2-hydroxypropylamine (acid-base titration). Here, the reaction mixture reacted to the point of a 2-hydroxypropylamine content of 0.8% by weight.

Example 3: Synthesis of
N,N-di(2-hydroxyethyl)-12-hydroxystearamide 875.3 g (0.94 mol) of hydrogenated castor oil were mixed as described under Example 1 with 295.1 g (2.81 mol) of N,N-di(2-hydroxyethyl)amine. 15 g of a 30% strength by weight sodium methanolate solution were added to this reaction mixture and stirring was carried out for 3 hours at 110° C. The reaction control was carried out via the determination of the free N,N-(di-2-hydroxyethyl)amine. Here, the reaction mixture reacted as far as a N,N-di(2-hydroxyethyl)amine content of 4.0% by weight.

Example 4: Synthesis of
N-(2-aminoethyl)-12-hydroxystearamide 561 g (0.6 mol) of hydrogenated castor oil were reacted as described under Example 1 with 541 g (9.0 mol) of 2-aminoethylamine and 14 g of a 30% strength by weight sodium methanolate solution. When amidation is complete, the excess ethylenediamine is distilled off at 160° C./20 mbar. The resulting amide has a residual content of 7.4% 2-aminoethylamine.

Example 5: Synthesis of
N-2-(2-hydroxyethoxy)ethyl-12-hydroxystearamide 882.3 g (0.943 mol) of hydrogenated castor oil were reacted as described under Example 1 with 297.4 g (2.83 mol) of N-2-(2-hydroxyethoxy)ethylamine and 18 g of a 30% strength by weight sodium methanolate solution. Here, the reaction mixture reacted as far as a residual amine content of 4.6% by weight.

Example 6: Synthesis of N-(2,3,4,5,6-pentahydroxyhexyl)-12-hydroxystearamide 374 g (0.4 mol) of hydrogenated castor oil were reacted as described under Example 1 with 234.2 g (1.2 mol) of N-(2,3,4,5,6-pentahydroxyhexyl)amine and 9 g of a 30% strength by weight sodium methanolate solution. Here, the reaction mixture reacted as far as a residual amine content of 5% by weight.

Example 7: Synthesis of N—(N,N-dimethyl-3-aminopropyl)-12-hydroxystearamide 374.2 g (0.40 mol) of hydrogenated castor oil were initially introduced at 90° C. and dried for 30 min at a vacuum of 50 mbar. The vacuum was then broken with nitrogen, and 0.25 g of hypophosphorous acid (50% strength by weight in water) and 159.4 g (1.560 mol) of N,N-dimethyl-3-aminopropylamine were added. The reaction mixture was stirred for 3 h at 120° C. The reaction control was carried out by IR spectroscopy, the reaction being converted until the ester bands had completely disappeared. The temperature was then increased to 140° C. and the excess N,N-dimethyl-3-aminopropylamine was distilled off at a vacuum of 20 mbar. This gave 496 g of N—(N,N-dimethyl-3-aminopropyl)-12-hydroxystearamide.

Example 8: N-(2-Hydroxyethyl)-12-hydroxystearamide

An aqueous composition of 3% by weight of N-(2-hydroxyethyl)-12-hydroxystearamide and 10% by weight of a linear alkylbenzenesulphonate neutralized with monoethanolamine was prepared and heated with stirring (magnetic stirrer core) to 80° C. until a homogeneous solution was present. The mixture was then slowly cooled to room temperature with stirring (cooling rate ~2° C. per minute). 33% by weight of this mixture were incorporated into a detergent composition according to Table 1 such that a 1% strength by weight formulation of N-(2-hydroxyethyl)-12-hydroxystearamide was obtained:

TABLE 1

| Ingredient | % by weight |
| --- | --- |
| Linear alkylbenzenesulphonate | 9.0 |
| C12-14 fatty alcohol ethoxylate | 4.5 |
| C12-18 fatty acid | 3.8 |
| C12-14 dimethylamine oxide | 1.5 |
| Citric acid | 1.5 |
| 1,2-Propanediol | 3.8 |
| Boric acid | 0.4 |
| Ethanol | 1.1 |
| Water | to 100% |
| Monoethanolamine | to pH = 8.0 |

The formulation has, as shown in FIG. 1, shear-thinning properties in the rheology test.

Example 9: N-(2-Hydroxypropyl)-12-hydroxystearamide

Figure 2:
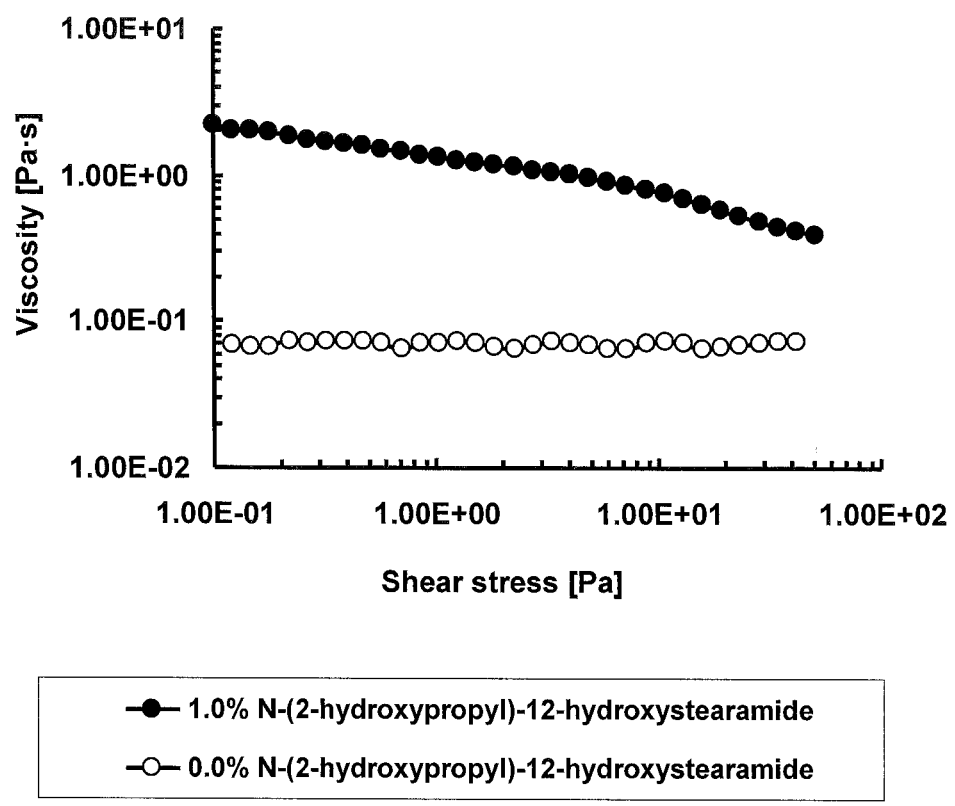

An aqueous composition of 4% by weight of N-(2-hydroxypropyl)-12-hydroxystearamide and 19.1% by weight of a linear alkylbenzenesulphonate neutralized with monoethanolamine was produced and heated with stirring (magnetic stirrer core) to 80° C. until a homogeneous solution was present. The mixture was then cooled slowly with stirring to room temperature (cooling rate (~2° C. per minute). 25% by weight of this mixture were incorporated into a detergent composition according to Table 1 such that a 1% strength by weight formulation of N-(2-hydroxypropyl)-12-hydroxystearamide was obtained. The formulation has, as shown in FIG. 2, shear-thinning properties in the rheology test.

In an alternative procedure, N-(2-hydroxypropyl)-12-hydroxystearamide was incorporated directly into the example formulation according to Table 1 until an end concentration of 1.00% by weight was established. The formulation was heated with stirring (magnetic stirrer core) to 80° C. and cooled slowly with stirring to room temperature (cooling rate ~2° C. per minute).

Figure 3:
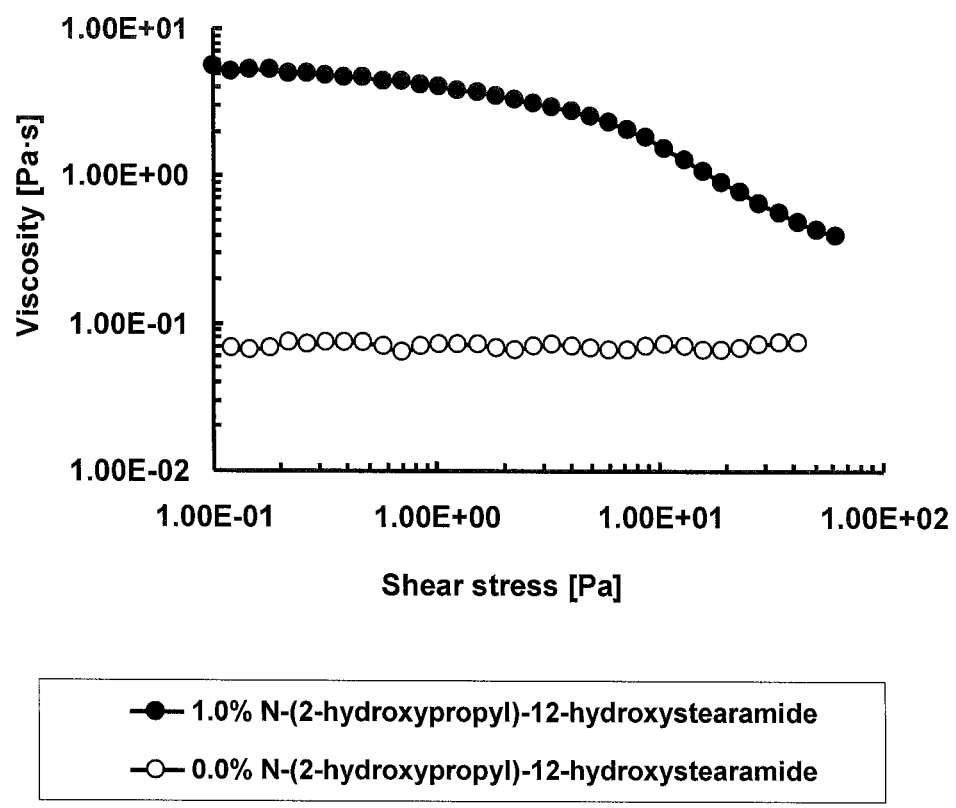

Here too, the formulation has, as shown in FIG. 3, shear-thinning properties in the rheology test.

Example 10: N-(2-Aminoethyl)-12-hydroxystearamide 1.5% by weight of N-(2-aminoethyl)-12-hydroxystearamide were incorporated into the detergent formulation described in Table 1. The formulation was heated with stirring (magnetic stirrer core) to 80° C. and cooled slowly with stirring to room temperature (cooling rate ~2° C. per minute). As shown in FIG. 4, the formulation has shear-thinning properties in the rheology test.

Example 11: N—(N,N-Dimethyl-3-aminopropyl)-12-hydroxystearamide

Figure 5:
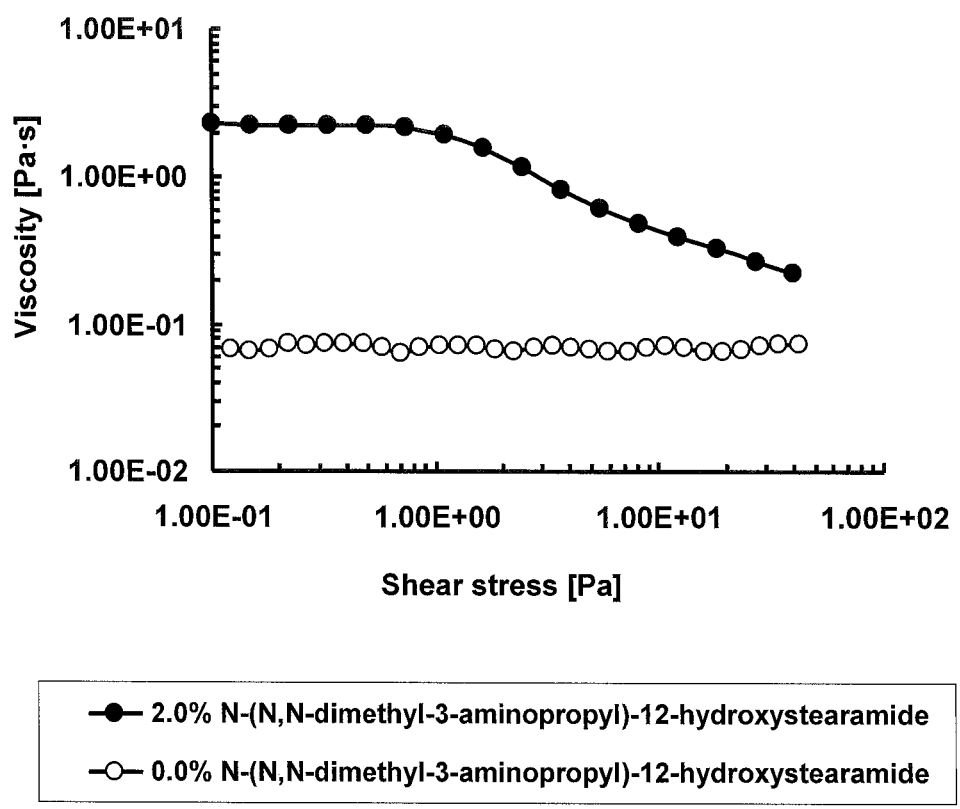

An aqueous, hydrochloric solution (pH=1) of 3.5% by weight of N—(N,N-dimethyl-3-aminopropyl)-12-hydroxystearamide was prepared at room temperature with slow stirring (magnetic stirrer core). The detergent composition described in Table 1 was incorporated into this solution such that an end concentration of 2% by weight of N—(N,N-dimethyl-3-aminopropyl)-12-hydroxystearamide, based on the total formulation, was obtained. Then, the pH of the formulation was adjusted to pH=8 with monoethanolamines, during which a significant increase in the viscosity of the formulation could be observed. As shown in FIG. 5, the formulation has shear-thinning properties in the rheology test.

Example 12: N-(2,3,4,5,6-Pentahydroxyhexyl)-12-hydroxystearamide

Figure 6:
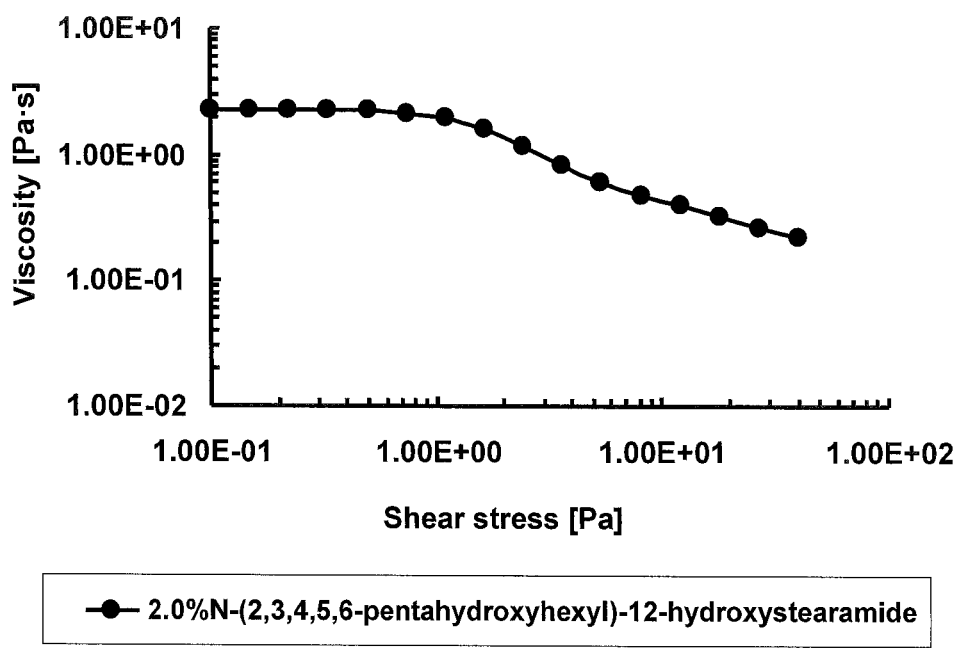

An aqueous composition of 2% by weight of N-(2,3,4,5,6-pentahydroxyhexyl)-12-hydroxystearamide was produced and heated with stirring (magnetic stirrer core) to 80° C. until a homogeneous solution was present. The mixture was then cooled slowly with stirring to room temperature (cooling rate (~2° C. per minute). As shown in FIG. 6, the formulation has shear-thinning properties in the rheology test.

Example 13: Comparative Example: Hydrogenated Castor Oil

An aqueous composition of 4% by weight of hydrogenated castor oil and 19.1% by weight of a linear alkylbenzenesulphonate neutralized with monoethanolamine was produced and heated with stirring (magnetic stirrer core) to 80° C. until a homogeneous solution was present. The mixture was then cooled slowly with stirring to room temperature (cooling rate (~2° C. per minute).

Figure 7:
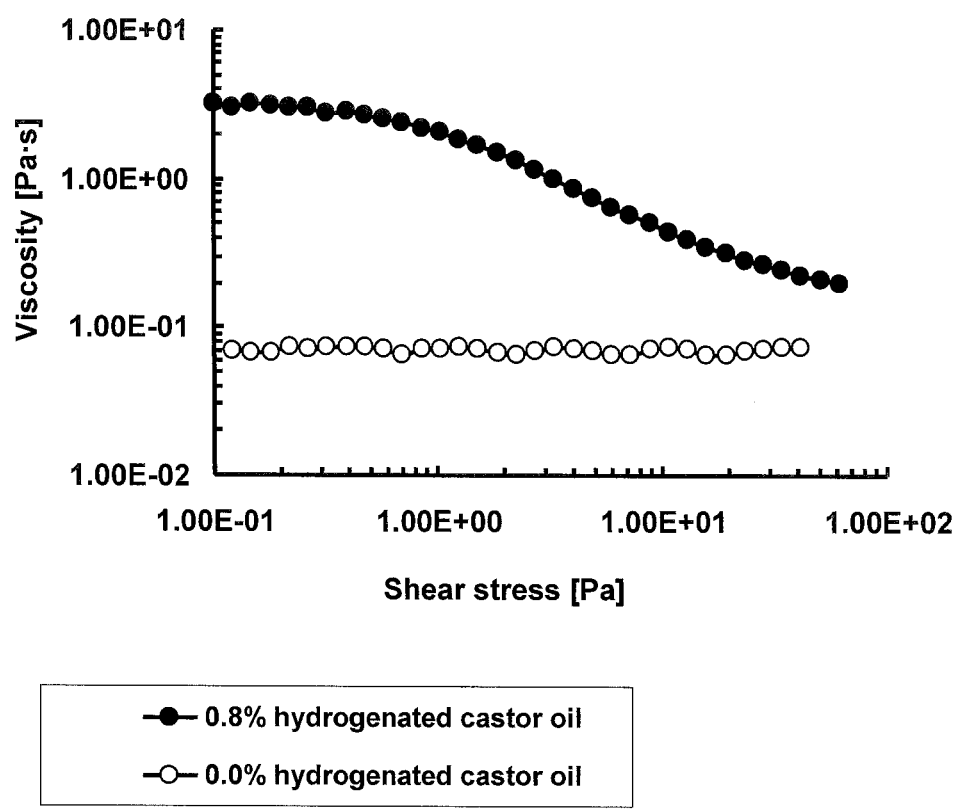

20% by weight of this mixture were incorporated into a detergent composition according to Table 1 such that a 0.8% strength by weight formulation of hydrogenated castor oil was obtained. The formulation has, as shown in FIG. 7, shear-thinning properties in the rheology test.

Example 14: Lipase stability of N-(2-hydroxypropyl)-12-hydroxystearamide

Figure 8A:
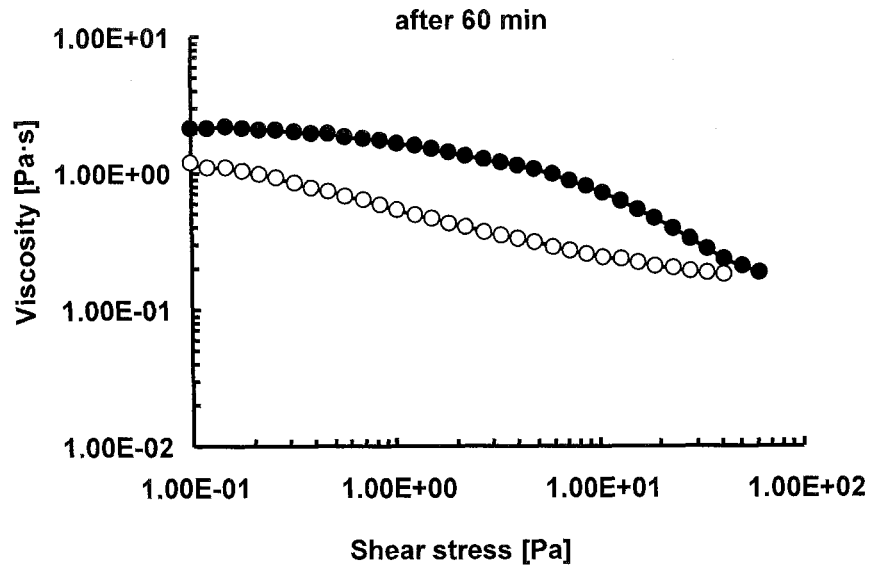
Figure 8B:
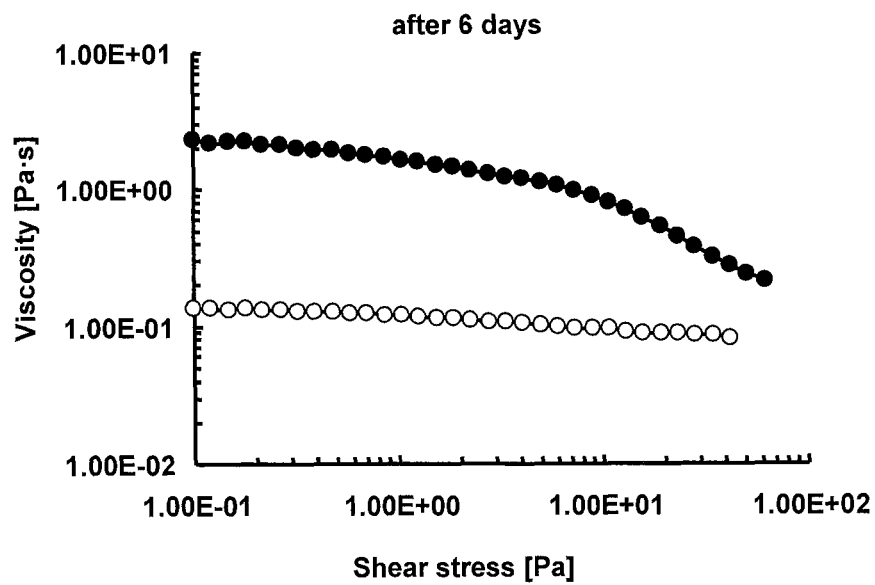

1% by weight of lipase (lypozyme) was added to the first-mentioned example formulation of Example 2. The comparison formulation used was the formulation described in the comparative example to which 1% by weight of lipase was likewise added. The rheology behaviour of the formulations was recorded one hour and six days after mixing; as shown in FIGS. 8a and b, the thickening property of the hydrogenated castor oil breaks down completely after six days, whereas N-(2-hydroxypropyl)-12-hydroxystearamide retains its total activity.

Example 15: Thickening of a Biosurfactant Formulation

The following formulations were prepared and their viscosities were measured using a Brookfield viscometer LVT, equipped with spindle 2, at 30 rpm and a temperature of 25° C.:

SL=Sophorolipid from Ecover.
LAS=MARLON ARL from Sasol, sodium (n-C10-C13-alkylbenzenesulphonate)

| LAS [% by wt.] | SL [% by wt.] | N-(2-Hydroxyethyl)-12-hydroxystearamide [% by wt.] | Viscosity [mPas] |
|---|---|---|---|
| 4.5 | 4.5 | 0 | 25 |
| 4.5 | 4.5 | 1 | 1000 |
| 8.9 | 0.1 | 1 | 2500 |
| 8.1 | 0.9 | 1 | 3000 |
| 6.8 | 2.2 | 1 | 7500 |

The results show that the compound according to the invention is able to thicken a biosurfactant formulation.

Example 16: Formulation Examples

The formulation examples given in Tables 2 to 29 below show exemplary representatives of a large number of possible formulations according to the invention.

If the preparation of the formulation requires the separate preparation and/or mixing of formulation constituents beforehand, this is referred to as multiphase preparation.

If a two-phase preparation is required, the two phases are labelled as A and B in the tables given. In the case of three-phase processes, the three phases are labelled A, B and C. Unless stated otherwise, the data are data in % by weight.

In the examples listed, the corresponding 12-hydroxystearamide is always incorporated into the end formulation at a temperature of 80° C.

TABLE 2

| Formulation Example 1, Shampoo, PEG- & sulphate-free | |
|---|---|
| REWOTERIC ® AMC, Evonik Goldschmidt GmbH, 32% strength, (INCI:Sodium Cocoamphoacetate) | 15.00 |
| REWOPOL ® SB F 12 P, Evonik Goldschmidt GmbH, 96% strength, (INCI: Disodium Lauryl Sulfosuccinate) | 3.80 |
| Perfume | 0.30 |
| Water | 65.10 |
| TEGO ® Betain F 50, Evonik Goldschmidt GmbH, 38% strength, (INCI: Cocamidopropyl Betaine) | 13.00 |
| ANTIL ® HS 60, Evonik Goldschmidt GmbH, (INCI: Cocamidopropyl Betaine; Glyceryl Laurate) | 1.00 |
| Citric Acid, 30% strength | q.s. |
| Preservative | 0.30 |
| N-(N,N-dimethyl-3-aminopropyl)-12-hydroxystearamide | 1.5 |

TABLE 3

| Formulation Example 2, mild hair and body cleanser | |
|---|---|
| Plantacare ® 1200 UP, Cognis, 50% strength, (INCI: Lauryl Glucoside) | 11.40 |
| Plantacare ® 818 UP, Cognis, 51% strength, (INCI: Coco Glucoside) | 5.60 |
| Water | 63.00 |
| TEGOSOFT ® LSE 65 K SOFT, Evonik Goldschmidt GmbH, (INCI: Sucrose Cocoate) | 1.50 |
| TECO ® Betain F 50, Evonik Goldschmidt GmbH, 38% strength, (INCI: Cocamidopropyl Betaine) | 18.00 |
| Perfume, preservative | q.s. |
| Citric Acid, 30% | q.s. |
| N-(2-hydroxypropyl)-12-hydroxystearamide | 0.50 |

TABLE 4

| Formulation Example 3, moisturizing skin cleanser | | |
|---|---|---|
| A | TEXAPON ® NSO, Cognis, 28% strength, (INCI: Sodium Laureth Sulfate) | 30.00 |
| | Perfume | 0.30 |
| B | Water | 54.80 |
| | TEGOCEL ® fluid, HPM, 4000, Evonik Goldschmidt, GmbH, (INCI: Hydroxypropyl Methylcellulose) | 1.20 |
| | TEGO ® Betain C 60, Evonik Goldschmidt GmbH, 46% strength, (INCI: Cocamidopropyl Betaine) | 8.10 |
| | TEGOSOFT ® APM, Evonik Goldschmidt GmbH, (INCI: PPG-3 Myristyl Ether) | 1.00 |
| | TEGO ® Pearl N 300, Evonik Goldschmidt GmbH, (INCI: Glycol Distearate; Laureth-4; Cocamidopropyl Betaine) | 2.00 |
| | REWODERM ® LI S 80, Evonik Goldschmidt GmbH, (INCI: PEG-200 Hydrogenated Glyceryl Palmate; PEG-7 Glyceryl Cocoate) | 1.00 |
| | Preservative | 0.60 |
| | Citric Acid, 30% strength | q.s. |
| | N-(2-hydroxypropyl)-12-hydroxystearamide | 1.00 |

TABLE 5

| Formulation Example 4, shower gel | |
|---|---|
| TAGAT ® CH 40, Evonik Goldschmidt GmbH, (INCI: PEG-40 Hydrogenated Castor Oil) | 2.50 |
| Perfume | 0.30 |
| TEXAPON ® NSO, Cognis, 28% strength, (INCI: Sodium Laureth Sulfate) | 42.90 |
| Water | 39.30 |
| TEGO ® Betain F 50, Evonik Goldschmidt GmbH, 38% strength, (INCI: Cocamidopropyl Betaine) | 10.70 |

TABLE 5-continued

Formulation Example 4, shower gel

| | |
|---|---|
| LACTIL ®, Evonik Goldschmidt GmbH, (INCI: Sodium Lactate; Sodium PCA; Glycine; Fructose; Urea; Niacinamide; Inositol; Sodium Benzoate; Lactic Acid) | 1.00 |
| ANTIL ® 171, Evonik Goldschmidt GmbH (INCI: PEG-18 Glyeryl Oleate/Cocoate) | 2.00 |
| Preservative | 0.30 |
| N-(2-aminoethyl)-12-hydroxystearamide | 1.00 |

TABLE 6

Formulation Example 5, shower gel

| | |
|---|---|
| TEXAPON ® NSO, Cognis, 28% strength, (INCI: Sodium Laureth Sulfate) | 37.00 |
| Perfume | 0.30 |
| Water | 42.00 |
| REWOTERIC ® AMC, Evonik Goldschmidt GmbH, 32% strength, (INCI: Sodium Cocoamphoacetate) | 9.00 |
| TEGO ® Betain 810, Evonik Goldschmidt GmbH, strength, (INCI: Capryl/Capramidopropyl Betaine) | 7.60 |
| LACTIL ®, Evonik Goldschmidt GmbH, (INCI: Sodium Lactate; Sodium PCA; Glycine; Fructose; Urea; Niacinamide; Inositol; Sodium Benzoate; Lactic Acid) | 1.00 |
| Citric Acid, 30% strength | 1.30 |
| REWODERM ® LI S 80, Evonik Goldschmidt GmbH, (INCI: PEG-200 Hydrogenated Glyceryl Palmate; PEG-7 Glyceryl Cocoate) | 0.50 |
| Preservative | 0.30 |
| N-(2-aminoethyl)-12-hydroxystearamide | 1.00 |

TABLE 7

Formulation Example 6, shampoo, PEG- & sulphate-free

| | |
|---|---|
| REWOTERIC ® AM C, Evonik Goldschmidt GmbH, 32% strength, (INCI: Sodium Cocoamphoacetate) | 15.00 |
| Plantapon ACG 50, Cognis (INCI: Disodium Cocoyl Glutamate) | 3.80 |
| Perfume | 0.30 |
| Water | 66.30 |
| TEGO ® Betain F 50, Evonik Goldschmidt GmbH, 38% strength, (INCI: Cocamidopropyl Betaine) | 10.00 |
| VARISOFT ® PATC, Evonik Goldschmidt (INCI: Palmitamidopropyltrimonium Chloride) | 2.30 |
| REWOMID ® SPA, Evonik Goldschmidt GmbH, (INCI: Isostearamide MIPA) | 1.00 |
| Preservative | 0.30 |
| Citric Acid, 30% strength | q.s. |
| N-(2-hydroxypropyl)-12-hydroxystearamide | 1.00 |

TABLE 8

Formulation Example 7, shower gel

| | |
|---|---|
| TEXAPON ® NSO, Cognis, 28% strength (INCI: Sodium Laureth Sulfate) | 15.00 |
| Perfume | 0.30 |
| PGFAC-S, Cognis (INCI: Sodium cocoyl hydrolyzed wheat protein glutamate) | 1.50 |
| REWOPOL SB CS 50 B, Evonik Goldschmidt GmbH, 40% strength, (INCI: Disodium PEG-5 Lauryl Citrate Sulfosuccinate; Sodium Laureth Sulfate) | 7.50 |
| Water | 59.10 |
| TEGO ® Betain F 50, Evonik Goldschmidt GmbH, 38% strength, (INCI: Cocamidopropyl Betaine) | 9.00 |
| TEGO ® Betain 810 Evonik Goldschmidt GmbH 38% strength, (INCI: Capryl/Capramidopropyl Betaine) | 4.00 |
| ANTIL ® 200, Evonik Goldschmidt GmbH, (INCI: PEG-200 Hydrogenated Glyceryl Palmate; PEG-7 Glyceryl Cocoate) | 1.80 |

TABLE 8-continued

Formulation Example 7, shower gel

| | |
|---|---|
| Preservative | 0.30 |
| N-(N,N-dimethyl-3-aminopropyl)-12-hydroxystearamide | 1.50 |

TABLE 9

Formulation Example 8, shampoo, PEG- & sulphate-free

| | | |
|---|---|---|
| A | REWOTERIC ® AMC, Evonik Goldschmidt GmbH, 32% strength, (INCI: Sodium Cocoamphoacetate) | 20.00 |
| | REWOPOL ® SB F 12 P, Evonik Goldschmidt, 96% strength, (INCI: Disodium Lauryl Sulfosuccinate) | 5.90 |
| B | Water | 65.90 |
| | Citric Acid, 30% strength | 3.60 |
| C | ANTIL ® HS 60, Evonik Goldschmidt GmbH, (INCI: Cocamidopropyl Betaine; Glyceryl Laurate) | 3.00 |
| | Preservative | 0.60 |
| | N-(N,N-dimethyl-3-aminopropyl)-12-hydroxystearamide | 1.00 |

TABLE 10

Formulation Example 9, body cleanser

| | | |
|---|---|---|
| A | TEXAPON ® NSO Cognis 28% strength, (INCI: Sodium Laureth Sulfate) | 30.00 |
| | ABIL ® B 8832, Evonik Goldschmidt GmbH, (INCI: Bis-PEG/PPG-20/20 Dimethicone) | 0.30 |
| | Perfume | 0.30 |
| B | Water | 52.50 |
| | TEGOCEL ® fluid HPM 4000, Evonik Goldschmidt GmbH, (INCI: Hydroxypropyl Methylcellulose) | 1.20 |
| | Citric Acid Monohydrate | 0.50 |
| | REWOTERIC ® AM C, Evonik Goldschmidt GmbH, 32% strength, (INCI: Sodium Cocoamphoacetate) | 10.00 |
| | TECO ® Pearl N 300, Evonik Goldschmidt GmbH, (INCI: Glycol Distearate; Laureth-4; Cocamidopropyl Betaine) | 2.00 |
| | REWODERM ® LI S 80, Evonik Goldschmidt GmbH, (INCI: PEG-200 Hydrogenated Glyceryl Palmate; PEG-7 Glyceryl Cocoate) | 1.60 |
| | Preservative | 0.60 |
| | Citric Acid, 30% strength | q.s. |
| | N-(2-hydroxypropyl)-12-hydroxystearamide | 1.00 |

TABLE 11

Formulation Example 10, sprayable hair milk, PEG-free

| | | |
|---|---|---|
| A | Water | 95.30 |
| | Lactic Acid, 80% strength | 0.40 |
| B | TEGO ® AMID S 18, Evonik Goldschmidt GmbH, (INCI: Stearamidopropyl Dimethylamine) | 1.20 |
| | TEGIN ® G 1100 Pellets, Evonik Goldschmidt GmbH, (INCI: Glycol Distearate) | 0.60 |
| | TECO ® Care PS, Evonik Goldschmidt GmbH, (INCI: Methyl Glucose Sesquistearate) | 1.20 |
| | TEGOSOFT ® DEC, Evonik Goldschmidt GmbH, (INCI: Diethylhexyl Carbonate) | 0.30 |
| | Perfume, preservative | q.s. |
| | N-(2-aminoethyl)-12-hydroxystearamide | 1.00 |

TABLE 12

Formulation Example 11, body cleansing foam

| | |
|---|---|
| TEXAPON ® NSO, Cognis, 28% strength (INCI: Sodium Laureth Sulfate) | 14 |
| Perfume | 0.3 |
| REWOTERIC ® AM C, Evonik Goldschmidt GmbH, 32% strength (INCI: Sodium Cocoamphoacetate) | 8 |
| Water | 75.0 |

TABLE 12-continued

Formulation Example 11, body cleansing foam

| | |
|---|---|
| TEGOCEL ® HPM 50, Evonik Goldschmidt GmbH (INCI: Hydroxypropyl Methylcellulose) | 0.5 |
| LACTIL ® Evonik Goldschmidt GmbH (INCI: Sodium Lactate; Sodium PCA; Glycine; Fructose; Urea; Niacinamide; Inositol; Sodium Benzoate; Lactic Acid) | 1 |
| Citric Acid Monohydrate | 0.5 |
| N-(2-hydroxypropyl)-12-hydroxystearamide | 0.7 |

TABLE 13

Formulation Example 12, conditioning shampoo

| | |
|---|---|
| TEXAPON ® NSO, Cognis, 28% strength (INCI: Sodium Laureth Sulfate) | 32.00 |
| VARISOFT ® PATC, Evonik Goldschmidt GmbH (INCI: Palmitamidopropyltrimonium Chloride) | 1.50 |
| REWODERM ® LI S 80, Evonik Goldschmidt GmbH (INCI: PEG-200 Hydrogenated Glyceryl Palmate; PEG-7 Glyceryl Cocoate) | 2.00 |
| Perfume | 0.25 |
| Water | 53.75 |
| TEGO ® Cosmo C 100, Evonik Goldschmidt GmbH, (INCI: Creatine) | 1.00 |
| Jaguar C-162, Rhodia (INCI: Hydroxypropyl Guar Hydroxypropyltrimonium Chloride) | 0.20 |
| TEGO ® Betain F 50, Evonik Goldschmidt GmbH, 38% strength (INCI: Cocamidopropyl Betaine) | 8.00 |
| NaCl | 0.50 |
| Preservative | q.s. |
| N-(2-hydroxypropyl)-12-hydroxystearamide | 0.80 |

TABLE 14

Formulation Example 13, pearlized shampoo

| | |
|---|---|
| TEXAPON ® NSO, Cognis, 28% strength (INCI: Sodium Laureth Sulfate) | 32.00 |
| Perfume | 0.25 |
| Water | 54.75 |
| TEGO ® Betain F 50, Evonik Goldschmidt GmbH, 38% strength (INCI: Cocamidopropyl Betaine) | 8.00 |
| TEGO ® Pearl N 300 Evonik Goldschmidt GmbH (INCI: Glycol Distearate; Laureth-4; Cocamidopropyl Betaine) | 2.00 |
| ANTIL ® 171 Evonik Goldschmidt GmbH (INCI: PEG-18 Glyceryl Oleate/Cocoate) | 1.50 |
| NaCl | 0.50 |
| Preservative | q.s. |
| N-(N,N-dimethyl-3-aminopropyl)-12-hydroxystearamide | 1.00 |

TABLE 15

Formulation Example 14, rinse-off conditioner

| | |
|---|---|
| Water | 90.00 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| TEGO ® Alkanol 1618, Evonik Goldschmidt GmbH (INCI: Cetearyl Alcohol) | 5.00 |
| Preservative, perfume | q.s. |
| N-(N,N-dimethyl-3-aminopropyl)-12-hydroxystearamide | 1.00 |

TABLE 16

Formulation Example 15, conditioning shampoo

| | |
|---|---|
| TEXAPON ® NSO, Cognis, 28% strength (INCI: Sodium Laureth Sulfate) | 32.00 |
| ANTIL ® 200, Evonik Goldschmidt GmbH (INCI: PEG-200 Hydrogenated Glyceryl Palmate; PEG-7 Glyceryl Cocoate) | 2.00 |
| Perfume | 0.25 |
| Water | 56.25 |
| Polymer JR 400, Amerchol (INCI: Polyquaternium-10) | 0.20 |
| TEGO ® Betain F 50, Evonik Goldschmidt GmbH, 38% strength (INCI: Cocamidopropyl Betaine) | 8.00 |
| NaCl | 0.30 |
| Preservative | q.s. |
| N-(2-hydroxypropyl)-12-hydroxystearamide | 1.00 |

TABLE 17

Formulation Example 16, moisturizing skin cleanser

| | | |
|---|---|---|
| A | TEXAPON ® NSO, Cognis, 28% strength, (INCI: Sodium Laureth Sulfate) | 30.00 |
| | Cap01 | 0.70 |
| | Perfume | 0.30 |
| B | Water | 55.10 |
| | TEGOCEL ® fluid HPM 4000, Evonik Goldschmidt GmbH, (INCI: Hydroxypropyl Methylcellulose) | 1.20 |
| | TEGO ® Betain C 60, Evonik Goldschmidt GmbH, 46% strength, (INCI: Cocamidopropyl Betaine) | 8.10 |
| | TEGOSOFT ® APM, Evonik Goldschmidt GmbH, (INCI: PPG-3 Myristyl Ether) | 1.00 |
| | Cutina TS, Cognis (INCI: PEG- 3 Distearate) | 1.00 |
| | REWODERM ® LI S 80, Evonik Goldschmidt GmbH, (INCI: PEG-200 Hydrogenated Glyceryl Palmate; PEG-7 Glyceryl Cocoate) | 1.00 |
| | Preservative | 0.60 |
| | Citric Acid, 30% strength | q.s. |
| | N-(2-hydroxypropyl)-12-hydroxystearamide | 1.00 |

TABLE 18

Formulation Example 17, shower gel

| | |
|---|---|
| TEXAPON ® NSO, Cognis, 28% strength (INCI: Sodium Laureth Sulfate) | 15.00 |
| Perfume | 0.30 |
| PGFAC-S, Cognis (INCI: Sodium cocoyl hydrolyzed wheat protein glutamate) | 1.50 |
| REWOPOL SB CS 50 B, Evonik Goldschmidt GmbH, 40% strength, (INCI: Disodium PEG-5 Lauryl Citrate Sulfosuccinate; Sodium Laureth Sulfate) | 7.50 |
| Water | 59.35 |
| TEGO ® Betain F 50, Evonik Goldschmidt GmbH, 38% strength, (INCI: Cocamidopropyl Betaine) | 9.00 |
| TEGO ® Betain 810, Evonik Goldschmidt GmbH, 38% strength, (INCI: Capryl/Capramidopropyl Betaine) | 4.00 |
| Polyquaternium- 7, Nalco, (INCI: Merquat 550) | 0.50 |
| ANTIL ® 200, Evonik Goldschmidt GmbH, (INCI: PEG-200 Hydrogenated Glyceryl Palmate; PEG-7 Glyceryl Cocoate) | 1.80 |
| Preservative | 0.30 |
| N-(2-hydroxypropyl)-12-hydroxystearamide | 0.75 |

TABLE 19

Formulation Example 18, body cleanser

| | | |
|---|---|---|
| A | TEXAPON ® NSO Cognis 28% strength, (INCI: Sodium Laureth Sulfate) | 30.00 |
| | ABIL ® B 8832, Evonik Goldschmidt GmbH, (INCI: Bis-PEG/PPG-20/20 Dimethicone) | 0.30 |
| | Perfume | 0.30 |
| B | Water | 52.50 |
| | TEGOCEL ® fluid HPM 4000, Evonik Goldschmidt GmbH, (INCI: Hydroxypropyl Methylcellulose) | 1.20 |
| | Citric Acid Monohydrate | 0.50 |
| | REWOTERIC ® AM C, Evonik Goldschmidt GmbH, 32% strength, (INCI: Sodium Cocoamphoacetate) | 10.00 |
| | Cutina TS, Cognis (INCI: PEG- 3 Distearate) | 2.00 |
| | REWODERM ® LI S 80, Evonik Goldschmidt GmbH, (INCI: PEG-200 Hydrogenated Glyceryl Palmate; PEG-7 Glyceryl Cocoate) | 1.60 |
| | Preservative | 0.60 |
| | Citric Acid, 30% strength | q.s. |
| | N-(2-aminoethyl)-12-hydroxystearamide | 1.00 |

TABLE 20

Formulation Example 19, body cleansing foam

| | |
|---|---|
| TEXAPON ® NSO, Cognis, 28% strength (INCI: Sodium Laureth Sulfate) | 14 |
| Perfume | 0.3 |
| REWOTERIC ® AM C, Evonik Goldschmidt GmbH, 32% strength (INCI: Sodium Cocoamphoacetate) | 8 |
| Water | 74.7 |
| TEGOCEL ® HPM 50, Evonik Goldschmidt GmbH (INCI: Hydroxypropyl Methylcellulose) | 0.5 |
| LACTIL ® Evonik Goldschmidt GmbH (INCI: Sodium Lactate; Sodium PCA; Glycine; Fructose; Urea; Niacinamide; Inositol; Sodium Benzoate; Lactic Acid) | 1 |
| Panthenol, BASF, (INCI: D- Panthenol USP) | 0.2 |
| Citric Acid Monohydrate | 0.5 |
| N-(2-hydroxypropyl)-12-hydroxystearamide | 0.8 |

TABLE 21

Formulation Example 20, rinse-off conditioner

| | |
|---|---|
| Water | 89.40 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| TEGO ® Alkanol 16, Evonik Goldschmidt GmbH (INCI: Cetyl Alcohol) | 5.00 |
| Preservative, perfume | q.s. |
| N-(N,N-dimethyl-3-aminopropyl)-12-hydroxystearamide | 1.6 |

TABLE 22

Formulation Example 21, rinse-off conditioner

| | |
|---|---|
| Water | 89.40 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |

TABLE 22-continued

Formulation Example 21, rinse-off conditioner

| | |
|---|---|
| TEGO ® Alkanol 18, Evonik Goldschmidt GmbH, (INCI: Stearyl Alcohol) | 5.00 |
| Preservative, perfume | q.s. |
| N-(N,N-Dimethyl-3-aminopropyl)-12-hydroxystearamide | 1.6 |

TABLE 23

Formulation Example 22, rinse-off conditioner

| | |
|---|---|
| Water | 88.40 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| TEGO ® Alkanol 1618, Evonik Goldschmidt GmbH (INCI: Cetearyl Alcohol) | 5.00 |
| DC 949, Dow Corning, (INCI: Amodimethicone) | 1.00 |
| Preservative, perfume | q.s. |
| N-(N,N-Dimethyl-3-aminopropyl)-12-hydroxystearamide | 1.6 |

TABLE 24

Formulation Example 23, rinse-off conditioner

| | |
|---|---|
| Water | 88.40 |
| VARISOFT ® EQ 65, Evonik Goldschmidt GmbH (INCI: Distearyl Dimonium Chloride, Cetearyl Alcohol) | 2.00 |
| VARISOFT ® BT 85, Evonik Goldschmidt GmbH (INCI: Behentrimonium Chloride) | 2.00 |
| TEGO ® Alkanol 1618, Evonik Goldschmidt GmbH (INCI: Cetearyl Alcohol) | 5.00 |
| DC 1503 Fluid, Dow Corning, (INCI: Dimethicone, Dimethiconol) | 1.00 |
| Preservative, perfume | q.s. |
| N-(N,N-dimethyl-3-aminopropyl)-12-hydroxystearamide | 1.6 |

TABLE 25

Formulation Example 24, turbid conditioning shampoo

| | |
|---|---|
| TEXAPON ® NSO, Cognis, 28% strength (INCI: Sodium Laureth Sulfate) | 32.00 |
| ANTIL ® 200, Evonik Goldschmidt GmbH (INCI: PEG-200 Hydrogenated Glyceryl Palmate; PEG-7 Glyceryl Cocoate) | 2.00 |
| Perfume | 0.25 |
| Water | 53.25 |
| Polymer JR 400, Amerchol (INCI: Polyquaternium-10) | 0.20 |
| TEGO ® Betain F 50, Evonik Goldschmidt GmbH, 38% strength (INCI: Cocamidopropyl Betaine) | 8.00 |
| DC1503 Fluid, Dow Corning, (INCI: Dimethicone, Dimethiconol) | 1.00 |
| TEGO ® Pearl N 300 Evonik Goldschmidt GmbH (INCI: Glycol Distearate; Laureth-4; Cocamidopropyl Betaine) | 2.00 |
| NaCl | 0.30 |
| Preservative | q.s. |
| N-(2-hydroxypropyl)-12-hydroxystearamide | 1.00 |

TABLE 26

Formulation Example 25, conditioning antidandruff sham

| | | |
|---|---|---|
| A | TEGIN ® G 1100 Pellets, Evonik Goldschmidt GmbH, (INCI: Glycol Distearate) | 3.00 |
| | TEXAPON ® NSO, Cognis, 28% strength (INCI: Sodium Laureth Sulfate) | 40.0 |

TABLE 26-continued

Formulation Example 25, conditioning antidandruff sham

| | | |
|---|---|---|
| B | Perfume | 0.30 |
| | Zinc- Pyrion NF, WeylChem, 48% strength | 2.00 |
| | (INCI: Zinc Pyrithione) | |
| | ABIL ® Quat 3272, Evonik Goldschmidt GmbH, | 1.00 |
| | (INCI: Quaternium- 80) | |
| C | Water | 37.4 |
| | TEGO ® Carbomer 341 ER, Evonik Goldschmidt GmbH, | 0.20 |
| | (INCI: Acrylates/C10-30 Alkyl Acrylate Crosspolymer) | |
| | Polymer JR 400, Amerchol, (INCI: Polyquaternium-10) | 0.30 |
| | NaOH, 25% strength | 0.30 |
| D | Rewoteric AM B U 185 ® Evonik Goldschmidt GmbH, | 12.5 |
| | (INCI: Undecylenamidopropyl Betaine) | |
| | Preservative | q.s |
| | N-(2-hydroxypropyl)-12-hydroxystearamide | 3.00 |

TABLE 27

Formulation Example 26, conditioning antidandruff sham

| | | |
|---|---|---|
| A | TEGIN ® G 1100 Pellets, Evonik Goldschmidt GmbH, | 3.00 |
| | (INCI: GlycoDistearate) | |
| | TEXAPON ® NSO, Cognis, 28% strength | 40.0 |
| | (INCI: Sodium Laureth Sulfate) | |
| B | Perfume | 0.30 |
| | Crinipan AD, Haarmann & Reimer Fragrance | 0.30 |
| | GmbH (INCI: Climbazole) | |
| | ABIL ® Quat 3272, Evonik Goldschmidt | 1.00 |
| | GmbH, (INCI: Quaternium- 80) | |
| C | Water | 39.1 |
| | TEGO ® Carbomer 341 ER, Evonik Goldschmidt GmbH, | 0.20 |
| | (INCI: Acrylates/C10-30 Alkyl Acrylate Crosspolymer) | |
| | Polymer JR 400, Amerchol, (INCI: Polyquaternium-10) | 0.30 |
| | NaOH, 25% strength | 0.30 |
| D | Rewoteric AM B U 185 ® Evonik Goldschmidt GmbH, | 12.5 |
| | (INCI: Undecylenamidopropyl Betaine) | |
| | Preservative | q.s |
| | N-(2-hydroxypropyl)-12-hydroxystearamide | 3.00 |

TABLE 28

Formulation Example 27, conditioning antidandruff sham

| | | |
|---|---|---|
| A | TEGIN ® G 1100 Pellets, Evonik Goldschmidt GmbH, | 3.00 |
| | (INCI: Glycol Distearate) | |
| | TEXAPON ® NSO, Cognis, 28% strength | 40.0 |
| B | Perfume | 0.30 |
| | Zinc-Pyrion NF, WeylChem, 48% strength | 2.00 |
| | (INCI: Zinc Pyrithione) | |
| | ABIL ® Quat 3272, Evonik Goldschmidt GmbH, | 1.00 |
| | (INCI: Quaternium- 80) | |
| C | Water | 37.1 |
| | TEGO ® Carbomer 140, Evonik Goldschmidt | 0.50 |
| | GmbH, (INCI: Carbomer) | |
| | Polymer JR 400, Amerchol, (INCI: Polyquaternium-10) | 0.30 |
| | NaOH, 25% strength | 0.30 |
| D | Rewoteric AM B U 185 ® Evonik Goldschmidt GmbH, | 12.5 |
| | (INCI: Undecylenamidopropyl Betaine) | |
| | Preservative | q.s |
| | N-(2-hydroxypropyl)-12-hydroxystearamide | 3.00 |

TABLE 29

Formulation Example 28, conditioning antidandruff sham

| | | |
|---|---|---|
| A | TEGIN ® G 1100 Pellets, Evonik Goldschmidt GmbH, | 3.00 |
| | (INCI: Glycol Distearate) | |
| | TEXAPON ® NSO, Cognis, 28% strength | 40.0 |
| | (INCI: Sodium Laureth Sulfate) | |
| B | Perfume | 0.30 |
| | Piroctone Olamine, Clariant (INCI: Octoprirox) | 0.30 |
| | ABIL ® Quat 3272, Evonik Goldschmidt GmbH, | 1.00 |
| | (INCI: Quaternium- 80) | |
| C | Water | 39.1 |
| | TEGO ® Carbomer 341 ER, Evonik Goldschmidt GmbH, | 0.20 |
| | (INCI: Acrylates/C10-30 Alkyl Acrylate Crosspolymer) | |
| | Polymer JR 400, Amerchol, (INCI: Polyquaternium-10) | 0.30 |
| | NaOH, 25% strength | 0.30 |
| D | Rewoteric AM B U 185 ® Evonik Goldschmidt GmbH, | 12.5 |
| | (INCI: Undecylenamidopropyl Betaine) | |
| | Preservative | q.s |
| | N-(2-hydroxypropyl)-12-hydroxystearamide | 3.00 |

The invention claimed is:

1. An aqueous formulation comprising a compound of formula (I)

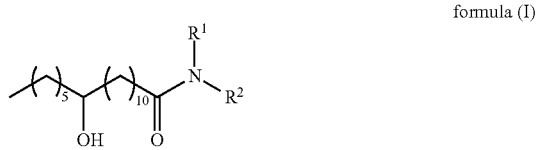

formula (I)

wherein $R^1$ and $R^2$ of the compound of formula (I) are selected from one of the following groupings $R^1$=H or 2-hydroxypropyl and $R^2$=2-hydroxypropyl;

$R^1$=H or 2-aminoethyl and $R^2$=2-aminoethyl;

$R^1$=H or N-(2-hydroxyethyl)aminoethyl and $R^2$=N-(2-hydroxyethyl)aminoethyl;

$R^1$=H or 2-(2-hydroxyethoxy)ethyl and $R^2$=2-(2-hydroxyethoxy)ethyl;

$R^1$=methyl or 2,3,4,5,6-pentahydroxyhexyl and $R^2$=2,3,4,5,6-pentahydroxyhexyl; and $R^1$=H or 2-(1-piperazinyl)ethyl and $R^2$=2-(1-piperazinyl)ethyl.

2. The aqueous formulation of claim 1, wherein $R^1$=H and $R^2$=N-(2-hydroxyethyl)aminoethyl.

3. The aqueous formulation according to claim 1, wherein said aqueous formulation further comprises at least one surfactant.

4. The aqueous formulation according to claim 3, wherein the at least one surfactant is a mixture of at least one anionic surfactant and at least one nonionic surfactant.

5. The aqueous formulation according to claim 3, wherein the at least one surfactant is a biosurfactant selected from rhamnolipids, sophorolipids, trehalose- and other mycolic-acid-containing glycolipids, and also cellobiose and mannosylerythritol lipids.

6. The aqueous formulation according to claim 1, wherein said aqueous formulation further comprises at least one enzyme.

7. The aqueous formulation according to claim 1, wherein said at least one compound of formula (I) is present in an amount of from 0.1% by weight to 50% by weight, where the % by weight refers to the total formulation.

* * * * *